United States Patent
Hossainy

(10) Patent No.: US 7,922,760 B2
(45) Date of Patent: Apr. 12, 2011

(54) IN SITU TRAPPING AND DELIVERY OF AGENT BY A STENT HAVING TRANS-STRUT DEPOTS

(75) Inventor: Syed F. A. Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 491 days.

(21) Appl. No.: 11/807,856

(22) Filed: May 29, 2007

(65) Prior Publication Data

US 2008/0300669 A1    Dec. 4, 2008

(51) Int. Cl.
*A61F 2/06* (2006.01)
(52) U.S. Cl. ............... 623/1.42; 623/1.43; 623/1.15
(58) Field of Classification Search .......... 623/1.15, 623/1.16, 1.34, 1.42; 424/423; 604/96
See application file for complete search history.

(56) References Cited

U.S. PATENT DOCUMENTS

| | | | |
|---|---|---|---|
| 5,893,840 A * | 4/1999 | Hull et al. | ............ 604/103.02 |
| 7,115,299 B2 | 10/2006 | Kokish | |
| 2002/0007209 A1 * | 1/2002 | Scheerder et al. | ............ 623/1.15 |
| 2005/0186241 A1 | 8/2005 | Boyle et al. | |
| 2007/0255206 A1 * | 11/2007 | Reneker et al. | ............ 604/96.01 |

FOREIGN PATENT DOCUMENTS

WO    WO 03/037221    5/2003

OTHER PUBLICATIONS

International Search Report for PCT/US2008/062947, mailed Jul. 30, 2008, 14 pgs.

* cited by examiner

*Primary Examiner* — Corrine M McDermott
*Assistant Examiner* — Seema Swaminathan
(74) *Attorney, Agent, or Firm* — Squire, Sanders & Dempsey (US) LLP

(57) ABSTRACT

A method of delivering an agent into a bodily lumen, the method comprising: implanting an implantable medical device into a treatment site of a lumen, the device having an abluminal face and a luminal face, wherein the device includes depots that extend from an open end at a luminal face to an open end at an abluminal face; and introducing an agent into the open end of the depots at the luminal face such that the agent is delivered to the treatment site through the open end at the abluminal face.

24 Claims, 3 Drawing Sheets

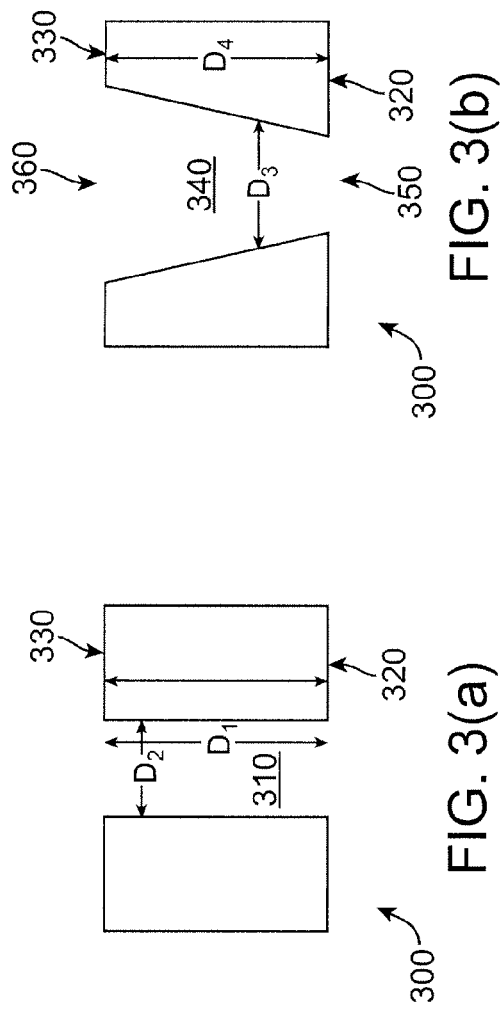
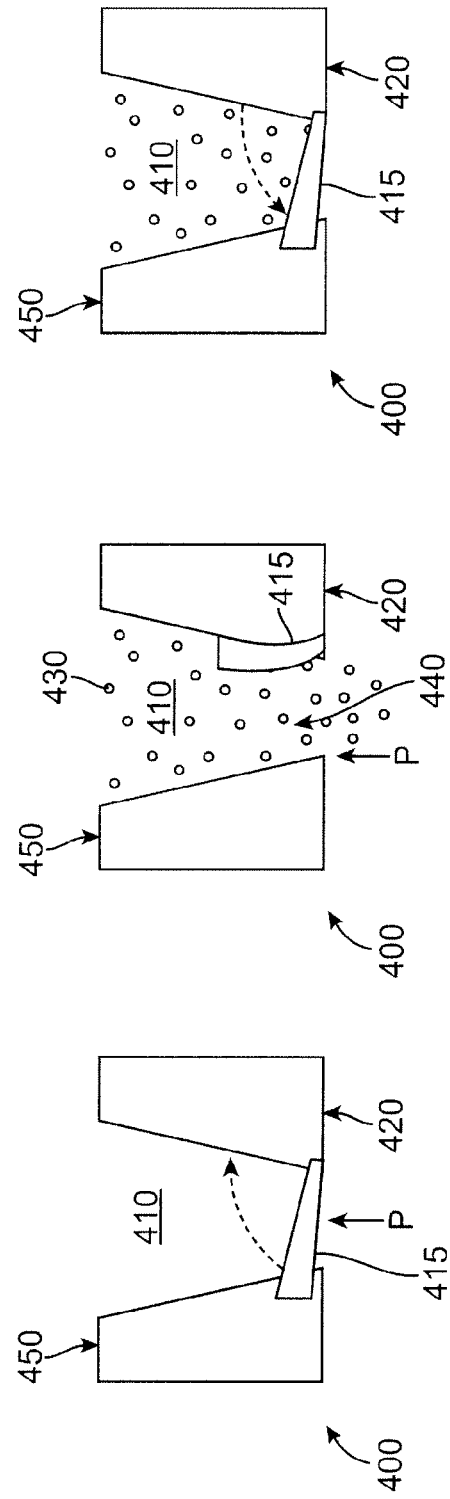

IN SITU TRAPPING AND DELIVERY OF AGENT BY A STENT HAVING TRANS-STRUT DEPOTS

BACKGROUND OF THE INVENTION

1. Field of the Invention

This invention relates to an implantable medical device, such as an expandable, intraluminal prosthesis commonly known as a stent. More particularly, this invention relates to a stent having depots formed in its cylindrical body, as well as a method of depositing agents, such as therapeutic agents, in the depots.

2. Description of the State of the Art

Percutaneous transluminal coronary angioplasty (PTCA) is a procedure for treating heart disease. An implantable medical device is introduced into the cardiovascular system of a patient via the brachial or femoral artery. The device is advanced through the coronary vasculature until the device is positioned across the occlusive lesion.

A problem associated with the procedure includes formation of intimal flaps or torn arterial linings which can collapse and occlude the conduit after the device is implanted. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an intraluminal prosthesis, an example of which includes an expandable stent, is implanted in the lumen to maintain the vascular patency. Stents are scaffoldings, usually cylindrical or tubular in shape, functioning to physically hold open, and if desired, to expand the wall of the passageway. Typically stents are capable of being compressed for insertion through small cavities via small catheters, and then expanded to a larger diameter once at the desired location.

In treating the damaged vasculature tissue and to further fight against thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of such medication often produces adverse or toxic side effects for the patient. Local delivery is a highly suitable method of treatment in that smaller levels of medication, as compared to systemic dosages, are concentrated at a specific site. Local delivery produces fewer side effects and achieves more effective results.

One commonly applied technique for the local delivery of the drugs is through the use of medicated stents. A proposed method involves the use of a polymeric carrier coated onto the body of the stent, as disclosed in U.S. Pat. No. 5,464,650 issued to Berg et al., U.S. Pat. No. 5,605,696 issued to Eury et al., U.S. Pat. No. 5,865,814 issued to Tuch, and U.S. Pat. No. 5,700,286 issued to Tartaglia et al. Obstacles often encountered with the use of a polymeric coating include difficulties in coating a complicated geometrical structure, poor adhesion of the polymeric coating to the surface of a stent, and biocompatibility of the polymer.

The art continues to develop more reliable ways to control the release profile of agents from a medical device or a coating. Such control can be important to obtain the desired effects or reduce any adverse effects that may otherwise occur from administration of the agents. In addition to providing a way to improve the bioactive, biobeneficial, and/or diagnostic results currently obtained from the administration of agents, control over the release rate of agents can assist in designing and maintaining the physical and mechanical properties of medical devices and coatings as well. Accordingly, control over the release of agents is an important design consideration and one of the next hallmarks in the development of stent technology.

SUMMARY

In accordance with various aspects of the present invention, an implantable prosthesis, one example of which includes a stent, is provided that is capable of being loaded with agents. The prosthesis is defined by a cylindrical shaped body having a thickness. Depots are formed on the body at preselected locations. The depots have a preselected depth and shape.

Disclosed is a method of delivering an agent into a bodily lumen, the method comprising: implanting an implantable medical device into a treatment site of a lumen, the device having an abluminal face and a luminal face, wherein the device includes depots that extend from an open end at a luminal face to an open end at an abluminal face; and introducing an agent into the open end of the depots at the luminal face such that the agent is delivered to the treatment site through the open end at the abluminal face. This allows for local delivery of the agent through the open end at the abluminal face.

Also disclosed is a method of delivering an agent into a lumen, the method comprising: implanting a stent into a treatment site of a lumen, the stent having an abluminal face and a luminal face, wherein the stent includes depots that extend from an open end at luminal face to an open end at abluminal face, and wherein the open end at the luminal face is narrower than the open end at the abluminal face; deploying a catheter having a balloon into the lumen, wherein upon inflation of the balloon, an agent is released from the balloon and is introduced into the open end of the depots at the luminal face; and removing the catheter having a balloon from the lumen. Again, as above, this allows for in situ application of the agent into the stent and in vivo, local delivery of the agent by the stent.

Also disclosed is a stent comprising: a body structure having a generally cylindrical shape, the body structure having an abluminal face and a luminal face; a plurality of depots that extend from an open end at luminal face to an open end at abluminal face; and a cover over each depot, the cover having an open position for allowing an agent to be introduced into the depots and a closed position.

BRIEF DESCRIPTION OF DRAWINGS

FIG. 3(a) depicts a cross-section of a trans-strut depot having a cylindrical shape.

FIG. 3(b) depicts a cross-section of a depot having a conical shape, where an opening on a depot at the luminal face is narrower than an opening at the abluminal face.

FIG. 4(a) depicts a cross-section of a depot having a uni-direction cover or valve in the closed position before an agent delivery implement transports the agent into the depot.

FIG. 4(b) depicts the depot of FIG. 4(a) in the open position when an agent delivery implement causes an agent to be introduced into the depot.

FIG. 4(c) depicts the depot of FIG. 4(a) in the closed position after an agent delivery implement is inactivated, causing the unidirectional cover to block the opening at the luminal face.

The features of the described embodiments are specifically set forth in the appended claims. However, the embodiments relating to both structure and method of operation are best understood by referring to the following description and accompanying drawings.

DETAILED DESCRIPTION

Embodiments disclose an agent-delivery system and a method of delivering an agent into a lumen. The method provides for implanting an implantable medical device, such as a stent, having depots that extend through the entire strut thickness of the stent. The stent can be a balloon-expandable stent, a self-expandable stent, or a stent-graft, all of which are well known in the art. A single depot or plurality of depots is formed on body of the stent. The depots are used for carrying a variety of agents including but not limited to therapeutic substances and polymers impregnated with therapeutic agents. The depots are loaded with the agent(s) such as therapeutic agent(s) using an agent delivery implement. After the agent delivery implement is removed, the stent releases the agent from the depots in a controlled, localized manner, which is absorbed into the tissue that is in contact with the stent. The surrounding tissues can also benefit from such a local application of agent(s).

Figure 1:
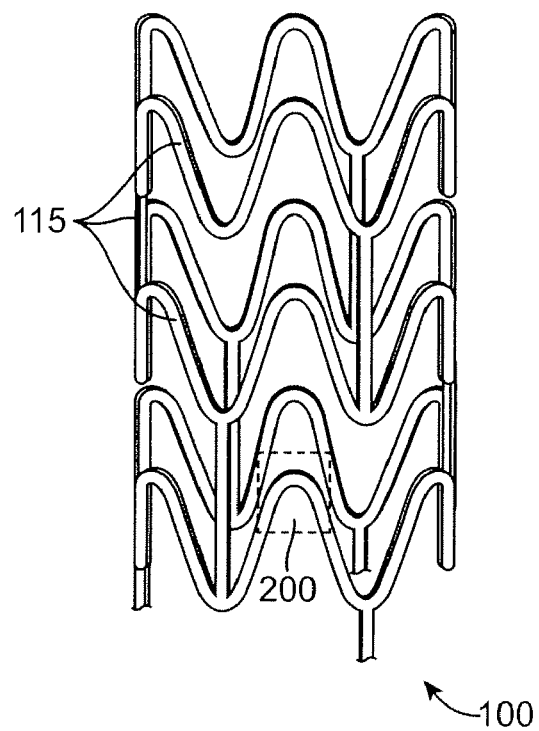
FIG. 1 depicts an example of a stent.

FIG. 1 depicts an example of a three-dimensional view of a stent 100. The stent may have a pattern that includes a number of interconnecting elements or struts 115. The embodiments disclosed are not limited to the stent structure or stent pattern depicted in FIG. 1. For example, the cross-section of a strut may be rectangular, (as depicted in FIG. 1), circular, oval, etc.

Figure 2:
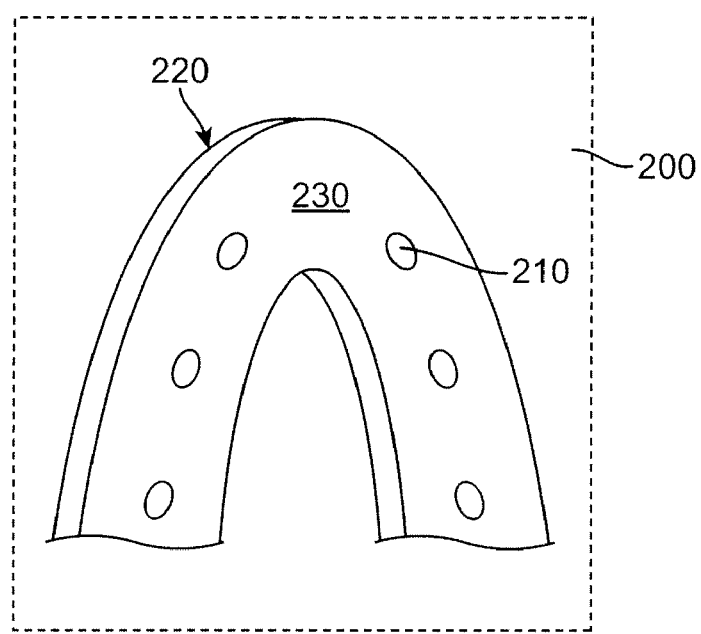
FIG. 2 depicts a section of the stent of FIG. 1 that includes trans-strut depots that extend from a luminal face to an abluminal face of the stent.

FIG. 2 depicts a section 200 of stent 100 from FIG. 1. Depots 210 advantageously extend through the entire thickness of the strut, or are "trans-strut" depots that extend from luminal or inner face 220 (lumen exposed surface) to abluminal or outer face 230 (tissue contacting surface). After stent 100 is implanted into a bodily lumen, depots 210 are loaded with an agent, in situ, by an agent delivery implement as will be described below. In some embodiments, agents can also be loaded during the stent implantation process, such as during the expansion on the stent.

FIGS. 3(a)-(b) depict a cross-section of a strut 300 having a depot 310 of trans-strut geometry, extending the entire thickness of strut, from a luminal face 320 to an abluminal face 330 of strut 300. The geometrical parameters that characterize depots such as size (e.g., depth, diameter, etc.) and shape may be configured to facilitate introduction of the agent into the depots.

Referring to FIG. 3(a), depot 310 may have a generally cylindrical shape. Depot 310 has a depth $D_1$ and diameter $D_2$.

The appropriate values for $D_1$ and $D_2$ may vary and depend on factors such as the effective amount of agent that needs to be delivered, mechanical integrity of the strut, density of depots or number of depots on the stent, and the desired release profile of agent. For instance, a larger depth $D_1$ and diameter $D_2$ may be used to increase the effective amount of agent released into the lumen. Furthermore, as the size and density of the depots increases, the mechanical strength of the strut may decrease.

FIG. 3(b) depicts a cross-section of a depot 340, which is substantially conical or reverse cone shape, having a narrower or cross-dimensional opening 350 at luminal face 320 than opening 360 at abluminal face 330. After the stent is implanted into the lumen, abluminal face 330 abuts against a lumen, and thus closes wider opening 360 of depot 340. An agent delivery implement is then implanted into a lumen to cause an agent to be introduced into opening 350 of depot at luminal face 320. Depots having a narrower opening 350 at luminal face 320 and a wider opening 360 at abluminal face 330 can have a variety of geometrical shapes other than the depicted conical shape. Further, although the diameter $D_3$ of conical-shaped depot 340 is depicted as gradually decreasing from abluminal face 330 to luminal face 320, other embodiments having a varying diameter $D_3$ are also possible. In one embodiment, the largest diameter of conical-shaped depot 340 is at the wider opening 360, as depicted in FIG. 3(b).

The opening 350 at luminal face 320 provides a channel by which an agent is introduced into the depot from an agent delivery implement. The narrower opening 350 has a diameter that is sufficiently wide enough to allow the agent to be introduced from the agent delivery implement.

In embodiments where the agent delivery implement is a balloon-catheter, the cone shape of depot 340 allows the agent to be introduced into opening 350 of the depots at luminal face 320 upon application of pressure by the balloon, while deterring the release of agent from opening 350 after pressure is reduced. The agent is deterred from release and is contained within the depots because of the shape of the depots as well as the decrease in pressure of the balloon after the agent is introduced into the depots. The narrower opening 350 of conical-shaped depot 340 constricts the depot at luminal face 320, thereby reducing or preventing the agent particles from exiting from luminal face 320. Thus, at luminal face 320, the agent is crowded against narrower opening 350, and at abluminal face 330, the agent is crowded against lumen.

In one embodiment, as depicted in FIGS. 4(a)-(c), a depot 410 in strut portion 400 includes a unidirectional cover, flap, or valve 415 that is connected to luminal face 420 of the stent, such that valve 415 covers narrower opening 440 of depot 410. The cover 415 can be generally positioned within the setting or inner rim of depots 40 as depicted in the figures. Although depicted with a conical depot, the cover 415 can be used with any shape depot. A balloon-catheter (not shown) is inserted adjacent to luminal face 420 and the balloon portion is inflated, such that pressure (depicted as "P") that is exerted from the balloon causes unidirectional cover 415 to open into depot 410, as depicted in FIG. 4(b). The pressure can be caused by the expansion of the balloon and/or secretion of the drug out of the balloon. An agent 430 that is released from the balloon is introduced into narrower opening 440 of depot 410, as depicted in FIG. 4(b). When the balloon is inactivated, unidirectional cover 415 returns to the closed position as depicted in FIG. 4(c). Unidirectional cover 415 serves to block opening 440 after pressure from the balloon is reduced. Thus, opening 440 at luminal face 420 is blocked by unidirectional cover 415, and the escape of agent 430 is prevented or reduced from opening 440 of depot 410.

The term "unidirectional" is meant to describe a cover that completely or substantially blocks the depot opening 440 at luminal face 420 when no pressure is being applied, but allows agent to enter opening 440 at luminal face 420 when pressure is applied. In one embodiment, unidirectional cover 415 opens into depot opening 440 when pressure is applied, and cover 415 returns to its natural state of blocking opening 440 or at least significantly preventing the escape of the agent from opening 440 when pressure decreases.

Unidirectional cover 415 can be fabricated of any material. For example, unidirectional cover 415 can be of a material such as hydrophilic polymeric material that is configured to increase release rate of hydrophilic agent from depot 415. Alternatively, cover 415 can be made of a hydrophobic polymer that is configured to increase the release rate of a hydrophilic agent. In some embodiments, a hydrophilic cover can be used with a hydrophilic agent or a hydrophobic cover can be used with a hydrophobic agent.

In one embodiment, a coating is applied over abluminal face 450 of the stent. In one aspect of this embodiment, the coating does not block opening 360 at abluminal face 330. The coating may also include an agent, such as an anti-inflammatory agent, that is delivered from the coating to treat an inflamed portion of a vessel. In some embodiments, the coating may block opening 30 at the abluminal face 330. Such a coating can be made of a biodegradable or bioerodable polymer which would provide a time release mechanism of the agent.

In another embodiment, the luminal face of the stent includes a coating, which may include an agent to be released into the blood stream.

Figure 5A:
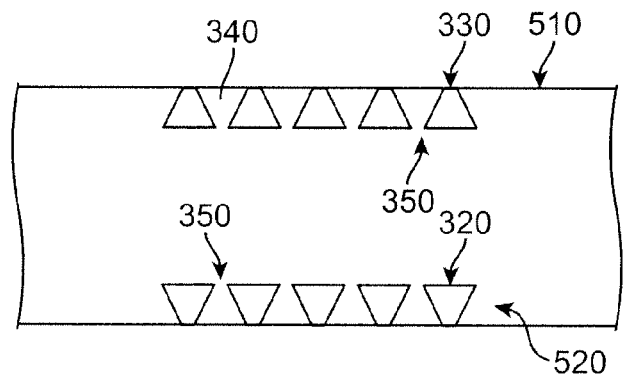
FIG. 5(a) depicts a stent implanted in lumen having trans-strut, conical-shaped depots.
Figure 5B:
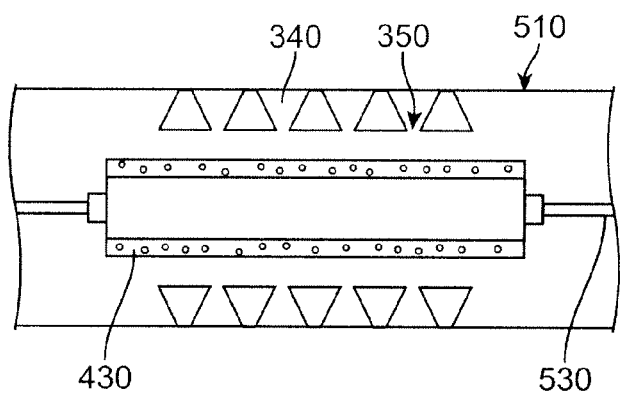
FIG. 5(b) depicts a balloon-catheter implanted in the treatment site prior to inflation of the balloon-catheter.

Turning now to FIGS. 5(a)-5(d), depicted is a cross-section of a portion of a lumen 510, having an implanted stent 520 according to one embodiment. As depicted, stent 520 includes conically-shaped depots 340 that are trans-strut from abluminal face 330 to luminal face 320 of stent in FIG. 5(a). In FIG. 5(b), a balloon-catheter 530 having an agent 430 is navigated into the treatment site. The balloon is positioned within stent 520 already implanted.

Any implement for delivering an agent(s) into the depots of stent 520 can be used. For example, the agent delivery implement may be an agent-loaded balloon-catheter, such as a balloon-catheter described in U.S. Pat. No. 7,115,299. The balloon-catheter may have, for example, a porous balloon that releases the agent upon the exertion of pressure, such as when the balloon is inflated. For example, the balloon can have an enclosed inner member for allowing the balloon to expand. A porous outer member can circumscribe the inner member. The agent can be introduced between the inner member and the porous outer member inflation of the inner member will cause the agent to be jetted out from the porous outer member. The embodiments are not limited to balloon-catheters, as other agent delivery implements and methods can be used to deliver the agent into the depots.

Figure 5C:
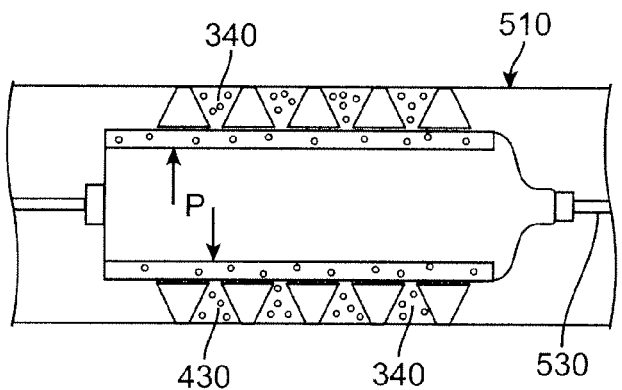
FIG. 5(c) depicts the balloon-catheter after inflation, causing an agent from the balloon to be released into the openings of the depots at the luminal face of the stent.
Figure 5D:
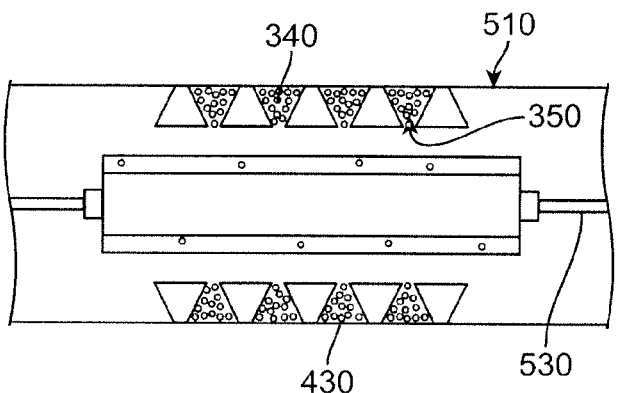
FIG. 5(d) depicts the depots loaded with agent after the balloon-catheter is inactivated.

In the embodiment depicted in FIG. 5(c), the balloon of the balloon-catheter 530 is expanded, and pressure from the balloon causes agent 430 to be introduced into openings 350 of conically-shaped depots 340 at luminal face 320. When pressure from agent delivery implement 530 is decreased and eliminated, as depicted in FIG. 5(d), agent 430 is prevented from being released from conical-shaped depot 340, and is thus contained in depots 340. The agent particles 540 are physically "bottle-necked" and prevented from escaping out from the depot and into the blood stream.

In some embodiments, the depot stent without any agents included in the depots can be crimped on a drug delivery balloon of a catheter. As the balloon is inflated to implant the stent, the stent is simultaneously loaded with the agent. The application of the agent can further continue for a short period after implantation to ensure that the depots have been adequately loaded. With this technique, an extra procedure of stent implantation is avoided.

The underlying structure or substrate of the stent can be completely or at least in part be made from a metal, an alloy, a biostable polymer or any combination.

A single depot or plurality of depots may be formed on a body of the stent by exposing a surface of the stent to an energy discharge from a laser, such as an excimer laser. Alternative methods of forming depots include, but are not limited to physical or chemical etching techniques. Depots can be formed in virtually any stent structure and not merely the above-described structure.

Numerous embodiments of stents with depots configured to release an active agent are possible. Depots may be placed at one or more selected locations on the stent. For example, in long lesions, the center portion of the lesion may be greater in need of an anti-inflammatory than the ends of the lesion. The greater inflammation may arise from a larger concentration of degradation products closer to the center of the stent than the ends of the stent. Thus, the center of the stent may contain more depots for use in releasing more anti-inflammatory agent than the ends of the device. Alternatively, the ends of the lesion may be more inflamed due to mechanical stresses causing irritation or injury from the stent. Thus, in some circumstances, a stent may include greater population of depots at its ends.

The stent according to the embodiments is useful for a variety of medical procedures, including, by way of example, treatment of obstructions caused by tumors in bile ducts, esophagus, trachea/bronchi and other biological passageways, and is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

The agent that is introduced into the depots can include one or more agents for treating a vascular disorder or a related disorder. The agent, for example, can be an anti-proliferative agent, an anti-inflammatory agent, and/or other bioactive agents.

The agent can also be included in particles that are introduced into the depots. The particles can be entirely made of agent(s). In one embodiment, the agent(s) is dispersed in a polymer. In one embodiment, the particles that are introduced into the depots are nanoparticles and/or microparticles.

There are numerous types of materials that can be used for particles that include agent. Representative examples of materials that may be used for particles include, but are not limited to, a biostable polymer; a bioabsorbable polymer; a biosoluble material; a biopolymer; a biostable metal; a bioerodible metal; a block copolymer of a bioabsorbable polymer or a biopolymer; a ceramic material such as a bioabsorbable glass; salts; fullerenes; lipids; carbon nanotubes; or a combination thereof. Particles may also include micelles or vesicles.

Particles may have active agents mixed, dispersed, or dissolved in the particle material. Particles may also be coated with an active agent. In other embodiments, particles have an outer shell of polymer, metal, or ceramic with inner compartment containing an active agent. In an embodiment, particles may include bioabsorbable glass with bioactive agent encapsulating or embedded within the particle. In some embodiments, particles are designed to use a combination of the above, e.g., a pure drug, a polymeric drug, or an agent impregnated core coated with a bioerodible metal. In addition, particles may include fullerenes coated with a bioactive agent. The size of the agent particles should be of a diameter smaller than the diameter of opening 350, so as to allow particles to be introduced into opening 350 of depot at luminal face. For example, the diameter of particles may range in diameter from 1% to 50% of the diameter of the openings 350, or more narrowly from 1% to 20% of the diameter of the openings 350.

The particles may have different treatment properties. The treatment properties may depend on type(s) of active agent included in each particle, release rate of active agents from the particle, degradation rate, size, and the like. Some particles may have different types of active agents, different release rates than other particles, different degradation rates, and different sizes.

The agent introduced into the depots of the stent can also be in the form of a composition or formulation of agent(s) that includes an agent and a fluid. The agent may be dispersed throughout the fluid or suspended in the fluid. The fluid used to make the agent composition can be virtually any fluid that is compatible with the agent. Therapeutic parameters such as the concentration of the agent in the fluid and dosages depend on a variety of factors including type of agent, type of fluid, concentration needed, and the like. Correlations and interrelations between the therapeutic parameters are well-known to one having ordinary skill in the art.

The invention advantageously provides a means for introducing an agent into the vessel wall simultaneously after the agent is delivered into the device's depots. In one embodiment, multiple treatments of agent are introduced into the depots at different time intervals. For example, one treatment of agent can be introduced and a different or the same treatment may be introduced six months or a year later.

Further, the invention provides flexibility as to the selection in size and shape of the agent. This is primarily due to the ability to directly introduce the agent into the depots, rather than having to incorporate the agent into a coating. For example, the agent need not have a particular size and property as do agents that are incorporated into a stent coating. The agent may also be easier to sterilize as compared to the process involved in sterilizing stents. Agents that are introduced into the stent depots according to the invention may also have a longer shelf life as compared to agents that are incorporated into a stent coating or a depot stent in which the agent is incorporated prior to the implantation procedure.

The term "agent(s)" that may be included in a composition, in a particle, or in a stent coating, refer to a variety of drug classes and therapeutic substances that may be used in accordance with embodiments described. For example, such drug classes and therapeutic substances can include, but are not limited to, one or more anti-proliferative agents that include, but is not limited to, rapamycin, ABT-578 (40-epi-(N1-tetrazolyl)-rapamycin), derivatives thereof, prodrugs thereof, metabolites thereof, everolimus (available under the trade name Certican™, Novartis Pharma AG, Germany), and/or combinations thereof, and anti-inflammatory agents such as clobetasol (available under the trade name Temovate™, Glaxosmithkline, UK). These bioactive agents can be a therapeutic, prophylactic, or diagnostic agent.

These agents can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

While the above listed agents are known for preventative and therapeutic use, the agents are listed by way of example and are not meant to be limiting. Other therapeutic substances are also applicable.

In general, polymers for use in fabricating the stent, the coating for the stent, or to provide an agent delivery particle can be biostable, bioabsorbable, biodegradable, or bioerodible. Biostable refers to polymers that are not biodegradable. The terms biodegradable, bioabsorbable, and bioerodible, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Representative examples of polymers that may be used to fabricate the stent, to coat the stent, or to provide an agent delivery particle include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of stents disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

In some embodiments, a stent may be formed from a tube by laser cutting the pattern of struts into the tube. The stent may also be formed by laser cutting a polymeric or metallic sheet, rolling the pattern into the shape of the cylindrical stent, and providing a longitudinal weld to form the stent. Other methods of forming stents are well known and include chemically etching a sheet and rolling and then welding it to form the stent. A polymeric or metallic wire may also be coiled to form the stent. The stent may be formed by injection molding of a thermoplastic or reaction injection molding of a thermoset polymeric material.

Disorders or conditions that can be treated by the stent include, but are not limited to, thrombosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, restenosis and progression of atherosclerosis in patient subsets including type I diabetics, type II diabetics, metabolic syndrome and syndrome X, vulnerable lesions including those with thin-capped fibroatheromatous lesions, systemic infections including gingivitis, hellobacteria, and cytomegalovirus, and combinations thereof.

Although a stent is the presently preferred application to the above embodiments, the embodiments are not limited to a stent and are applicable to other implantable medical devices. Implantable medical devices are any type of appliance that is totally or partly introduced, surgically or medically, into a patient's body or by medical intervention into a natural orifice, and which is intended to remain there after the procedure. Such devices include, without limitation, implantable cardiac pacemakers and defibrillators; leads and electrodes for the preceding; implantable organ stimulators such as nerve, bladder, sphincter and diaphragm stimulators; cochlear implants; prostheses; vascular grafts; self-expandable stents; balloon-expandable stents; stent-grafts; grafts; artificial heart valves and cerebrospinal fluid shunts.

While particular embodiments of the invention have been shown and described, it will be obvious to those skilled in the art that changes and modifications can be made without departing from this invention in its broader aspects and, therefore, the appended claims are to encompass within their scope all such changes and modifications as fall within the true spirit and scope of the invention.

The invention claimed is:

1. A method of delivering an agent into a bodily lumen, the method comprising:
    implanting an implantable medical device into a treatment site of a lumen, the device having an abluminal face and a luminal face, wherein the device includes depots that extend from an open end at a luminal face to an open end at an abluminal face; and
    during or after the implanting introducing an agent into the open end of the depots at the luminal face such that the agent is delivered to the treatment site through the open end at the abluminal face,
    wherein the introducing of the agent into the depots includes deploying an agent delivery catheter into the lumen, positioning the agent delivery catheter adjacent to the medical device, and delivering the agent by the agent delivery catheter into the depots.

2. The method according to claim 1, wherein the implantable medical device is a stent.

3. The method according to claim 1, wherein the open end of the depots on the luminal face is narrower than the open end of the depots at the abluminal face.

4. The method according to claim 1, wherein the medical device includes a polymeric coating on the abluminal surface of the medical device that covers the depots, does not cover the depots, or covers some depots but not all depots.

5. The method according to claim 4, wherein the polymeric coating includes an agent.

6. The method according to claim 1, wherein the agent comprises nanoparticles or microparticles.

7. The method according to claim 1, wherein the agent is in a particle form.

8. The method according to claim 1, wherein the introducing of the agent is performed after the implanting of the implantable medical device.

9. The method according to claim 1, wherein the agent delivery catheter includes a balloon.

10. The method according to claim 1, further comprising, after the introducing of the agent into the open end of the depots at the luminal face, allowing the agent to be released out from the open end of the depots at the abluminal face while simultaneously inhibiting the agent from releasing out from the open end of the depots at the luminal face.

11. A method of delivering an agent into a lumen, the method comprising:
    implanting a stent into a treatment site of a lumen, the stent having an abluminal face and a luminal face, wherein the stent includes depots that extend from an open end at the luminal face to an open end at the abluminal face, and wherein the open end at the luminal face is narrower than the open end at the abluminal face;

deploying a catheter having a balloon into the lumen, the deploying including inflating the balloon, wherein upon inflation of the balloon, an agent is released from the balloon and is introduced by the inflation into the open end of the depots at the luminal face; and removing the catheter from the lumen.

12. The method according to claim 11, wherein the shape of the depots is generally conical.

13. The method according to claim 11, wherein the agent is an anti-proliferative agent selected from the group consisting of everolimus, rapamycin, ABT-578 (40-epi-(N1-tetrazolyl)-rapamycin), derivatives thereof, prodrugs thereof, metabolites thereof, and/or combinations thereof.

14. The method according to claim 11, wherein the agent comprises nanoparticles or microparticles.

15. The method according to claim 11, wherein the agent is in a particle form.

16. The method according to claim 11, wherein the depots include a unidirectional cover.

17. The method according to claim 16, wherein the unidirectional covers are configured to cover the open end of the luminal face of the depots when no pressure is applied to the unidirectional covers, and upon inflation of the balloon, applied pressure from the inflation of the balloon causes the unidirectional covers to open and move into their respective depots to allow the introduction of the agent into the depots.

18. The method according to claim 17, wherein upon reduction of pressure of the balloon, the unidirectional covers are caused to cover the open end of the depots at the luminal face, preventing the agent from being released from the depots at the luminal face.

19. A stent comprising:

a body structure having a generally cylindrical shape, the body structure having an abluminal face and a luminal face;

a plurality of depots, each depot extending from an open end at the luminal face to an open end at the abluminal face; and a cover at the open end at the luminal face of each depot, the cover having an open position for allowing an agent to be introduced into the depots and a closed position, the covers configured to move within their respective depots.

20. The stent according to claim 19, wherein the implantable medical device is a stent.

21. The stent according to claim 19, wherein the open end of the depot on the luminal face is narrower than the open end of the depot at the abluminal face.

22. The stent according to claim 19, wherein the covers are configured to cover their respective open end at the luminal face and configured to move to an open position inside their respective depot in response to application of radially outward pressure at the luminal face.

23. The stent according to claim 19, wherein the covers are configured to move into their respective depots to achieve the open position.

24. The stent according to claim 19, wherein the covers are configured to move in a direction out of the their respective depots to achieve the closed position.

* * * * *